US009006171B2

(12) United States Patent
Nakahara et al.

(10) Patent No.: US 9,006,171 B2
(45) Date of Patent: Apr. 14, 2015

(54) ANGIOTENSIN CONVERTING ENZYME INHIBITORY PEPTIDE

(75) Inventors: Takeharu Nakahara, Noda (JP); Riichiro Uchida, Noda (JP); Hitomi Aota, Noda (JP); Katsutoshi Sugimoto, Noda (JP); Takuya Sato, Noda (JP)

(73) Assignee: Kikkoman Corporation, Chiba (JP)

( * ) Notice: Subject to any disclaimer, the term of this patent is extended or adjusted under 35 U.S.C. 154(b) by 352 days.

(21) Appl. No.: 13/120,531

(22) PCT Filed: Feb. 6, 2009

(86) PCT No.: PCT/JP2009/052108
§ 371 (c)(1),
(2), (4) Date: Mar. 23, 2011

(87) PCT Pub. No.: WO2010/082367
PCT Pub. Date: Jul. 22, 2010

(65) Prior Publication Data
US 2011/0171690 A1    Jul. 14, 2011

(30) Foreign Application Priority Data
Jan. 19, 2009  (JP) .................. 2009-008503

(51) Int. Cl.
C07K 5/083   (2006.01)
C07K 2/00    (2006.01)
C07K 5/065   (2006.01)
C07K 5/072   (2006.01)
C07K 5/078   (2006.01)
C07K 5/093   (2006.01)
A61K 38/00   (2006.01)

(52) U.S. Cl.
CPC . *C07K 2/00* (2013.01); *A61K 38/00* (2013.01); *C07K 5/06078* (2013.01); *C07K 5/06113* (2013.01); *C07K 5/06165* (2013.01); *C07K 5/06173* (2013.01); *C07K 5/0806* (2013.01); *C07K 5/0808* (2013.01); *C07K 5/0819* (2013.01)

(58) Field of Classification Search
CPC ...................................... C07K 5/083
See application file for complete search history.

(56) References Cited

U.S. PATENT DOCUMENTS

2004/0014670 A1  1/2004  Kodera et al.
2006/0217318 A1  9/2006  Wu et al.

FOREIGN PATENT DOCUMENTS

| CN | 1731934 | 2/2006 |
|---|---|---|
| JP | 04-91097 | 3/1992 |
| JP | 05-262790 | 10/1993 |
| JP | 05-339166 | 12/1993 |
| JP | 06-40944 | 2/1994 |
| JP | 07-188282 | 7/1995 |
| JP | 08-269087 | 10/1996 |
| JP | 10-175997 | 6/1998 |
| JP | 2002-053595 | 2/2002 |
| JP | 2006-75064 | 3/2006 |
| JP | 2007-008846 | 1/2007 |
| JP | 2007008846 A * | 1/2007 |
| JP | 2008-088151 | 4/2008 |
| JP | 2009-040696 | 2/2009 |
| WO | 02/055546 | 7/2002 |
| WO | 2004/082709 | 9/2004 |

OTHER PUBLICATIONS

Japanese Appl. No. JP 2007-008846 A, published Jan. 18, 2007, machine translation from the Japanese patent office, accessed Jul. 16, 2013, pp. 1-9.*
Vegners et al., "Synthesis and study of the biological activity of some arginine- and lysine-containing fragments of peptide hormones," Khim. Prir. Soedin. 9:516-24 (1973)—in Russian.*
Auna et al., "Results of a study of myotropic action of common fragments of some peptide hormones," Latvijas PSR Zinatnu Akademijas Vestis 7:104-9 (1975)—in Russian.*
PTO 13-5158, English translation of Auna et al., "Results of a study of myotropic action of common fragments of some peptide hormones," Latvijas PSR Zinatnu Akademijas Vestis 7:104-9 (1975).*
PTO 13-5153, English translation of Vegner et al.,Vegners et al., "Synthesis and study of the biological activity of some arginine- and lysine-containing fragments of peptide hormones," Khim. Prir. Soedin. 9:516-24 (1973).*
International Search Report for PCT/JP2009/052108 dated Apr. 28, 2009.
Wang, Wenyi et al., A New Frontier in Soy Bioactive Peptides that May Prevent Age-related Chronic Diseases, Comprehensive Reviews in Food Science and Food Safety, 4:63-78 (2005).
Kaitei Shinpan Shokuhin Kagaku (Revised New Edition Food Chemistry), Masao Fujimaki ed., Asakura Shoten, Mar. 1976, p. 117-118.
Database BIOSIS [Online], Biosciences Information Service, 1975, Auna, Z.P. et al., Results of a study of myotropic action of common fragments of some peptide hormones, XP00268916, Database accession No. PREV197661054425.
Database STN Chemical Abstracts [Online], Vegners, R. et al., Synthesis and study of the biological activity of some arginine- and lysine-containing fragments of peptide hormones, XP002055234, retrieved from Chemical Database accession No. 60189, published 1973.
Supplementary European Search Report dated Nov. 22, 2012, issued in corresponding European Application No. 09838334.2.
Japanese Office Action dated Aug. 22, 2013, issued in corresponding Japanese Patent Application No. 2009-008503, and English translation.
Chinese Office Action dated Oct. 21, 2013, issued in corresponding Chinese Patent Application No. 200980137462.5, and English translation.

* cited by examiner

*Primary Examiner* — Julie Ha
*Assistant Examiner* — Kristina M Hellman
(74) *Attorney, Agent, or Firm* — Roylance, Abrams, Berdo & Goodman, L.L.P.

(57) ABSTRACT

To provide ACE inhibitory peptides which can effectively inhibit ACE by a small amount of ingestion and have no fear of causing side effects and which can be orally ingested easily during daily life by persons having high blood pressure, and compositions comprising the peptides. The peptides represented by the following structural formulae (1) to (9), and salts thereof are provided. (1) Asp-Arg-Pro, (2) Asn-Trp, (3) Val-Gly-Leu, (4) Ile-Gly-Val, (5) Gly-Val-Pro, (6) Ile-Pro-Tyr, (7) pyroGlu-Pro, (8) Tyr-Thr, (9) Pro-Trp.

3 Claims, 2 Drawing Sheets

ANGIOTENSIN CONVERTING ENZYME INHIBITORY PEPTIDE

TECHNICAL FIELD

The present invention relates to peptides which exert a function of reducing blood pressure by inhibiting angiotensin converting enzyme, compositions comprising these peptides and production methods thereof.

BACKGROUND OF THE INVENTION

Angiotensin converting enzyme (to be referred to as ACE hereinafter) is a kind of carboxypeptidase exists in the animal body and produces angiotensin II by digesting one of the peptide bonds of angiotensin I. The angiotensin II is a peptide hormone having a strong vasopressor activity and causes hypertension through vasoconstriction, acceleration of aldosterone secretion and the like. Accordingly, inhibition of the ACE activity makes control of angiotensin II production and treatment of hypertension possible. Up to this time, medicaments such as captopril and the like have been put into practical use and broadly used as ACE inhibitors. However, since these medicaments have strong actions, there is a possibility of causing side effects and it is necessary to pay attention to side effects such as dry cough and the like in the case of many ACE inhibitors.

On the other hand, since the angiotensin I as the substrate of ACE is a peptide, studies have been carried out on the provision of a hypertension treating agent which competitively inhibits ACE by peptides derived from a natural source and shows no side effects (e.g., see Patent References 1 to 5). Since these peptides have mild actions, high safety is expected. On the other hand, there is a problem in that a peptide or a composition containing the peptide must be ingested in a relatively large amount in order to ingest its effective amount. Additionally, since many of these peptides have the whole hydrophobic property and it is considered that such peptides generally have strong bitterness (e.g., see Patent Reference 6, Non-patent References 1 and 2), there is also a problem of having a difficulty in orally taking them in a large amount.

Patent Reference 1: JP-A-4-091097
Patent Reference 2: JP-A-5-262790
Patent Reference 3: JP-A-6-040944
Patent Reference 4: JP-A-7-188282
Patent Reference 5: JP-A-10-175997
Patent Reference 6: JP-A-2006-75064
Non-patent Reference 1: Wenyi Wang et al., Comprehensive Reviews in Food Science and Food Safety, 2005, (4), p. 63-78
Non-patent Reference 2: "Kaitei Shinpan Shokuhin Kagaku (Revised New Edition Food Chemistry)" edited by Masao Fujimaki et al., Asakura Shoten, March, 1976, p. 117-118

DISCLOSURE OF THE INVENTION

Problems to be Solved by the Invention

A problem to be solved by the present invention is to provide ACE inhibitory peptides which effectively inhibit ACE by a small amount of ingestion; have no fear of causing side effects; and which can be orally ingested easily during daily life by persons having high blood pressure, compositions comprising the peptides and production methods thereof.

Means for Solving the Problems

With the aim of solving the above-mentioned problems, the inventors of the present invention have conducted intensive studies and found as a result peptides which have chemical structures (amino acid sequences) in which the presence of an ACE inhibitory action has not so far been known and have markedly strong action to accomplish the present invention. Namely, according to the present invention,

[1] Angiotensin converting enzyme inhibitory peptides represented by the following structural formulae (1) to (9):
(1) Asp-Arg-Pro, (2) Asn-Trp, (3) Val-Gly-Leu, (4) Ile-Gly-Val, (5) Gly-Val-Pro, (6) Ile-Pro-Tyr, (7) pyroGlu-Pro, (8) Tyr-Thr and (9) Pro-Trp and salts thereof;
[2] An angiotensin converting enzyme inhibitor, which comprises at least one of the peptides described in the above [1];
[3] A composition which comprises at least one of the peptides described in the above [1] and alleviates symptoms of high blood pressure; and
[4] A method for producing the peptides described in the above [1], wherein soybean is mixed and stirred at 25° C. or more with a *koji* fungus culture are provided.

Effect of the Invention

By the present invention, ACE inhibitory peptides which effectively inhibit ACE by a small amount of ingestion; have no fear of causing side effects; and show less bitterness and which can be orally ingested easily during daily life by persons having high blood pressure, compositions comprising these peptides and production methods thereof are provided.

BEST MODE FOR CARRYING OUT THE INVENTION

Figure 1:
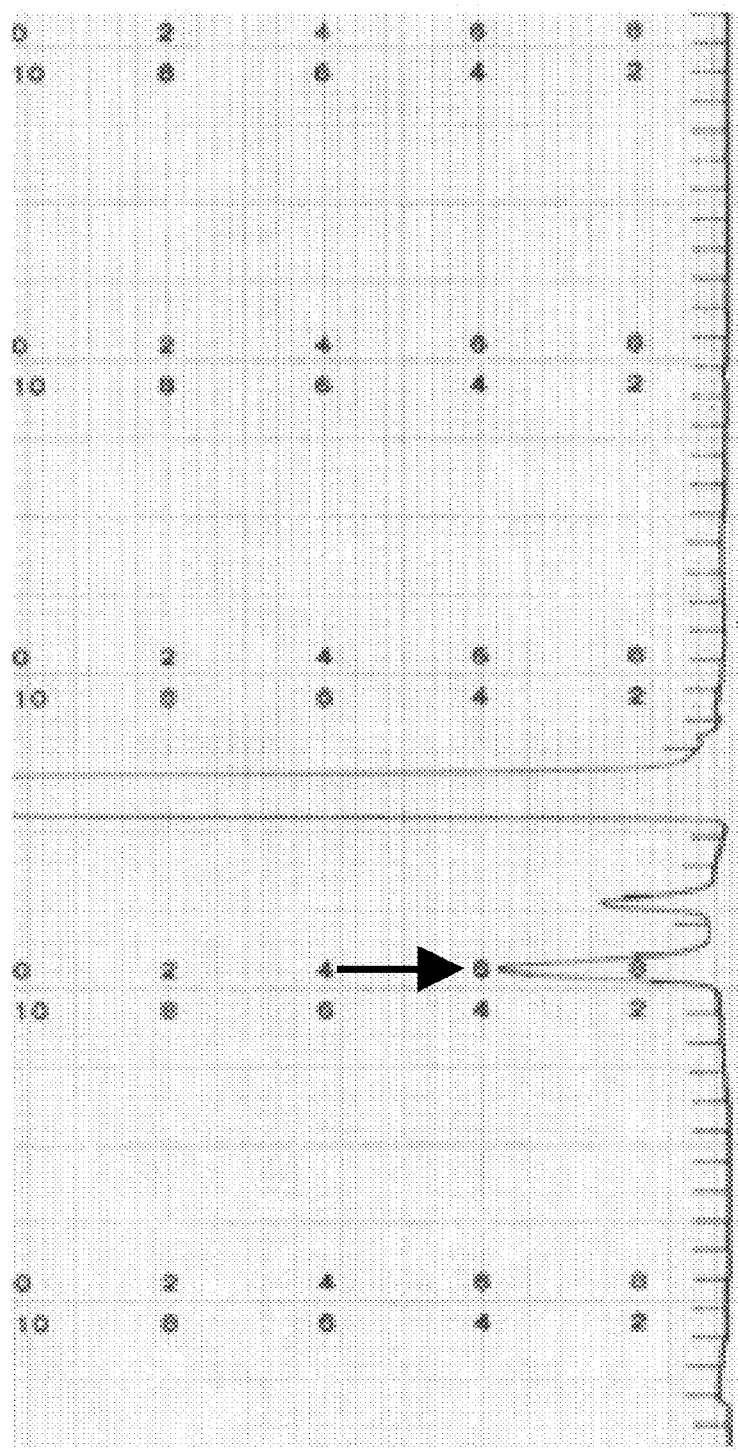
FIG. 1 is a figure showing a UV peak when Asp-Arg-Pro was isolated from a composition 1.

The following describes the present invention in detail.

The peptides of the present invention (1) Asp-Arg-Pro, (2) Asn-Trp, (3) Val-Gly-Leu, (4) Ile-Gly-Val, (5) Gly-Val-Pro, (6) Ile-Pro-Tyr, (7) pyroGlu-Pro, (8) Tyr-Thr and (9) Pro-Trp are dipeptides or tripeptides in which each amino acid residue was expressed by the generally used three letter code and pyroGlu represents pyroglutamic acid residue. These peptides can be produced, for example, by a chemically synthesizing method. As conventionally known methods, for example, there are a liquid phase method in which amino group of the amino terminus side amino acid is protected with a benzyloxycarbonyl group and the carboxyl group is activated with a p-nitrophenyl ester group and condensed with the carboxyl terminus side amino acid in the presence of triethylamine followed by removal of the protecting group by catalytic reduction or with trifluoroacetic acid and a solid phase method in which the carboxyl terminus side amino acid is bound to a polymeric solid phase support and amino acids after carrying out protection of amino group and activation of carboxyl group are bound thereto one by one by peptide binding followed by removal of the amino acid side chain protecting group by cutting out from the solid phase support using trifluoroacetic acid, hydrogen fluoride or the like. The production can be effected by both of the methods. In this connection, similar effects can be expected from not only a peptide simple substance but also its salt with a physiologically acceptable ion.

Additionally, the peptides of the present invention can also be produced using a column chromatography or the like, by separation and purification from a composition prepared by hydrolyzing a protein containing said amino acid sequence with an appropriate protease agent. In that case, the intended effect can be obtained even when ingested in the form of a composition containing said peptide. This is more desirable because mass production is easy and production cost is low, in comparison with the aforementioned chemical synthesis methods.

As the protein source in the case of obtaining the peptide of the present invention by hydrolysis of protein, although any material may be used as long as the object of the present invention can be achieved, preferably, it is suitable to use a leguminous plant. More preferably, it is desirable to use soybean from the viewpoints that its cultivation quantity is large; its cost is low; its protein content is large; its eating experience is rich; and taste of the composition after hydrolysis is good. The kind of soybean includes a yellow soybean, a red soybean, a black soybean and the like and a yellow soybean is particularly desirable. As the mode of soybean, whole soybean (whole fat soybean), defatted soybean, purified soybean protein and the like can be used as such or by applying an optional protein denaturation treatment after crushing and pulverization. As the protein denaturation treatment, the industrially broadly used pressure cooking is preferable.

As the protease agent in the case of obtaining the peptide of the present invention by hydrolysis of protein, although any material may be used as long as the object of the invention can be achieved, it is suitable to use a *koji* fungus culture from the viewpoints that its protease activity is high; its cost is low; its eating experience is rich; its safety is guaranteed; and taste of the composition after hydrolysis is good. As the *koji* fungus, *Aspergillus oryzae* and/or *Aspergillus sojae* is particularly suitable. These microorganisms have been used from ancient times for the protein degradation in fermentation production of soy sauce and soybean paste, and their safety has also been mentioned in the list of GRAS (Generally Recognized As Safe) and approved by Food and Drug Administration (FDA), USA. The *koji* fungus culture is a product obtained by inoculating and culturing a *koji* fungus using soybean, wheat, rice etc. as the medium. It is classified into a liquid *koji* culture and a solid *koji* culture based on the difference in culturing method and both cases can be used in the present invention. For example, a liquid *koji* culture can be obtained by inoculating a *koji* fungus into a liquid medium containing from 1% to 5% of soybean, wheat, wheat bran and the like and culturing it at from 25° C. to 40° C. for from 24 hours to 120 hours. Also, a solid *koji* culture mixture can be obtained by inoculating a *koji* fungus on a solid medium containing soybean, wheat and the like and culturing it at from 25° C. to 40° C. for from 24 hours to 120 hours.

As the conditions of the aforementioned hydrolysis reaction, from 10% to 70%, preferably from 30% to 50%, in final concentration of a *koji* fungus culture is mixed with from 5% to 40%, preferably from 15% to 30%, in final concentration of soybean; from 0% to 25%, preferably from 6% to 18%, in final concentration of salt; and further from 0% to 85% in final concentration of water, and final concentrations of soybean and salt are adjusted to the aforementioned ranges, followed by the reaction at from 25° C. to 60° C., preferably from 30° C. to 55° C., at an agitation rate of from 10 rpm to 150 rpm for from 12 hours to 240 hours, preferably from 24 hours to 168 hours. For the purpose of optionally improving flavor, it is possible to add a yeast strain belonging to the genus *Zygosaccharomyces* or the like and simultaneously carry out the fermentation.

Despite of containing the peptide of the present invention, the composition prepared by the aforementioned production method can be deliciously ingested as food because bitterness can hardly be felt and it has mellow and rich deliciousness and body and mild and superior aroma, which is and markedly different form the conventionally known ACE inhibitory peptide-containing compositions.

The methods for separating and purifying the peptide of the present invention from the aforementioned composition include ultrafiltration, dialysis, various types of chromatography and the like can be mentioned. These are generally broadly used methods. Particularly, a cation exchange chromatography and a reverse phase chromatography are effective from the viewpoint of treating amount of samples and purification efficiency.

The peptide of the present invention obtained in this manner can be used by oral or parenteral administration as an ACE inhibitor, namely a blood pressure increase inhibiting/reducing agent. In accordance with the usual way, it can be made into forms such as tablets, granules, powders, capsules and the like in the case of the oral administration, and can be made into forms such as injection preparations, percutaneous preparations, suppositories and the like in the case of parenteral administration.

Additionally, it can be used in food and drink for the purpose of preventing and/or treating hypertension (e.g., a healthy food, a health-conscious food, a functional food, a food for specified health uses and the like). The peptide of the present invention can be produced by adding it to various types of food and drink, and since its taste is good even in the form of a peptide-containing composition as described above, its addition to various types of food and drink is easy. Furthermore, it is also easy to ingest the composition itself. Examples of the food and drink obtained in this manner include soy sauce, soy sauce containing product, powder soy sauce, soybean paste, tsuyu and soups, broths, soybean milk, fermented milk, soft drink, concentrated drink stock liquid and adjusting powder, liquors, oil and fat-containing food, noodles, processed seafood, processed meat food, semi-solid food, pasty food, solid food and the like.

Although the dose of these peptides varies depending on the preventing or treating purpose and methods, within the range of from 0.01 mg to 100 mg as peptide per day is desirable. Additionally, in the case of ingesting it as a various types of food and drink, it is desirable that the ACE inhibitory activity represented by $IC_{50}$ becomes 1 mg/ml or less as a whole.

The following illustratively describes the present invention with reference to examples, the technical scope of the present invention is not limited to these examples.

Example 1

Production of Peptide by Chemical Synthesis Method

Production of Asn-Trp is exemplified in the following. In this connection, as the reagents other than the particularly mentioned ones, those produced by Wako Pure Chemical Industries, Ltd. were used. Firstly, 120 mg of L-tryptophan hydrochloride was dissolved in 2 ml of dimethylformamide, and 150 µl of triethylamine and 300 mg of Z-Asn-Onp (manufactured by KOKUSAN CHEMICAL Co., Ltd.) were added and stirred at room temperature for 24 hours. Next, 20 ml of 1% aqueous ammonia was added and allowed to stand at −10° C. for 1 hour. The formed precipitate was collected by filtration and the precipitate was washed with cold water. The precipitate was dissolved in 20 ml of methanol; 20 mg of palladium activated carbon was added thereto; and, after nitrogen gas sealing, a catalytic reduction reaction was carried out. The reaction was carried out at room temperature for 3 days by contacting with hydrogen gas while with under atmospheric pressure. After the reaction, the insoluble matter was removed by filtration and methanol was evaporated, followed by dissolution in distilled water. Next, fractionation purification was carried out by an ODS column (Cosmosil 5C18-ARII 20×250 mm, manufactured by Nakalai Tesque) connected to an HPLC (LC-8A, manufactured by Shimadzu Corp.). By using ultrapure water+0.1% trifluoroacetic acid (TFA) as the eluent A, and acetonitrile+0.1% TFA as the eluent B, gradient elution was carried out in accordance with the usual way. Each fraction was analyzed by a thin layer chromatography (TLC), and 87 mg of Asn-Trp was obtained from a fraction which showed a spot with a ninhydrin reagent. The chemical structure of it was confirmed in accordance with the usual way using a protein sequencer (Procise 492, manufactured by Applied Biosystems, Inc.), an NMR (AD-VANCE 500, manufactured by Bruker) and an LC-MS (1100, manufactured by Agilent Technologies and QSTAR Elite, manufactured by Applied Biosystems, the column was Develosil RPAQUEOUS-AR, manufactured by NOMURA CHEMICAL CO., LTD.).

ACE inhibitory activity of the peptides obtained by the aforementioned synthesis method was measured. As the measuring method, it was carried out by a method in which the method of Yamamoto et al. (Setsuko Yamamoto et al., Journal of the Japan Society of Chest Diseases, 1980, 18, p. 297-302) was partially modified. Namely, 140 µl of sample solution, 10 µl of enzyme solution (0.3 U/ml of ACE (rabbit lung-derived, manufactured by SIGMA) and 50 mM borate buffer (pH 8.3) were added to 100 µl of a substrate solution (12.5 mM Hippuryl-His-Leu (manufactured by SIGMA), 100 mM borate buffer pH 8.3, 1M NaCl), and the reaction was carried out at 37° C. for 30 minutes. Subsequently, the reaction was stopped by adding 250 µl of 1 N hydrochloric acid and, after stirring by adding 1.5 ml of ethyl acetate and subsequent centrifugation, 1 ml of the ethyl acetate layer was concentrated and dried by centrifugal concentration followed by dissolution in 1 ml of ultrapure water to measure the absorbance at 228 nm. The ACE inhibitory ratio is represented by the following formula.

ACE inhibitory ratio (%)={1−(ODs−ODsb)/(ODc−ODcb)}×100

In this connection, ODs is the absorbance when the reaction was carried out by adding the enzyme solution to a sample as described above; ODsb is the absorbance when ultrapure water was added instead of the enzyme solution; ODc is the absorbance when ultrapure water was added instead of the sample solution; and ODcb is the absorbance when ultrapure water was added instead of the enzyme solution and sample solution. Additionally, the concentration of a sample which gives 50% of the enzyme activity inhibitory ratio on this reaction system is regarded as the $IC_{50}$ value.

ACE inhibitory activities of the peptides of the present invention are shown in Table 1. In this connection, the $IC_{50}$ value of about 400 species of the main ACE inhibitory peptides so far reported was approximately from 1 µM to 1000 µM ("Shoku no Kagaku Library 3 Shokuhin Seibun no Hataraki (Science Library of Food 3 Action of Food Components)", edited by Koji Yamada, Asakura Shoten, March, 2004, p. 63-67). Since the peptides of the present invention have sufficiently strong activities in comparison with the conventionally known peptides, it is considered that they are industrially useful.

TABLE 1

| Amino Acid Sequences | ACE Inhibitory Activity ($IC_{50}$, µM) |
|---|---|
| Asp-Arg-Pro | 79 |
| Asn-Trp | 25 |
| Val-Gly-Leu | 257 |
| Ile-Gly-Val | 212 |
| Gly-Val-Pro | 100 |
| Ile-Pro-Tyr | 79 |
| pyroGlu-Pro | 106 |
| Tyr-Thr | 35 |
| Pro-Trp | 186 |

Example 2

Production of Peptide by a Method in which Soybean is Degraded with *Koji* Fungus Culture Mixture Spores of a *koji* fungus *Aspergillus sojae* were added to a solid medium containing equivalent amounts of heat-denatured whole soybean and wheat and cultured at from 25° C. to 40° C. for 72 hours to obtain a *koji* fungus culture. Next, 14 kg of heat-denatured whole soybean, 2 kg of *koji* fungus culture, 16 liters of water and 3 kg of salt were mixed and stirred at 100 rpm and at 45° C. for 5 days to obtain *moromi*. Next, a yeast strain: *Zygosaccharomyces rouxii* was mixed therewith at a ratio of $1.5 \times 10^6$ cells/ml and allowed to stand still at 25° C. for 7 days. Next, the insoluble solid matter was removed from the *moromi* using a hydraulic filter press to obtain a supernatant. By further carrying out enzyme deactivation and sterilization through heating at 117° C. for 5 seconds using an HS sterilizer (manufactured by HISAKA WORKS, LTD.) followed by standing still at 50° C. for 3 days, 20 liters of a supernatant alone containing no sediment was collected (composition 1).

By electrodialysis, 5 L of the composition 1 was desalted to about 0% salt and loaded on an ODS column (SP-120-40/60-ODS-B, manufactured by DAISO CO., LTD.) having a column volume of 18 liters. Using distilled water containing 0.1% TFA as the eluent A, and 30% acetonitrile containing 0.1% TFA as the eluent B and acetonitrile containing 0.1% TFA as the eluent C, linear gradient elution was carried out for 20 hours from A to B and then for 5 hours from B to C. By setting the flow rate to 45 ml/min, each 1600 ml fractions were obtained. Six fractions thereof were combined and concentrated by evaporator, and lyophilized to obtain a freeze-dried powder. The ACE inhibitory activity ($IC_{50}$ value) thereof was measured.

The above-mentioned freeze-dried powder was dissolved in ultrapure water and then loaded on an ODS column (Cosmosil 5C18-ARII 20×250 mm, manufactured by Nakalai Tesque) connected to a high performance liquid chromatography (HPLC, manufactured by Shimadzu Corporation). By using ultrapure water containing 0.1% TFA as the eluent A, and 70% acetonitrile containing 0.1% TFA as the eluent B, and after 10 minutes of holding with B: 0%, linear gradient elution was carried out for 70 minutes from B: 0% to B: 30% and then for 20 minutes until B: 100%. By setting the flow rate to 5 ml/min, each 7.5 ml fractions were obtained. After collecting 100 µl of sample was collected from each fraction, centrifugal concentration were carried out, followed by dissolution again in 500 μl of ultrapure water to measure the ACE inhibitory activity.

Furthermore, each fraction having the ACE inhibitory activity was loaded on a C30 column (Develosil RPAQUEOUS-AR 20×250 mm, manufactured by NOMURA CHEMICAL CO., LTD.). Using ultrapure water+0.1% TFA as the eluent A, and 40% acetonitrile+0.1% TFA as the eluent B, fractionation was carried out with a fraction size of 6 ml, at a flow rate of 5 ml/min under gradient conditions of (A 100%: 10 minutes)→(gradient until B 30%: 60 minutes)→(gradient until B 100%: 30 minutes). Its chromatogram is shown in FIG. 1. When the ACE inhibitory activity was measured, the activity was found only on the peak shown by arrow. When the fraction was concentrated by an evaporator and structural analysis using a protein sequencer, an NMR and an LC-MS was carried out, it was Asp-Arg-Pro. In the same manner, Asn-Trp, Val-Gly-Leu, Ile-Gly-Val, Gly-Val-Pro, Ile-Pro-Tyr and pyroGlu-Pro were isolated from other fractions.

Using the aforementioned LC-MS, the peptides of the present invention contained in the composition 1 were determined. Firstly, a calibration curve was prepared using a peptide obtained by a chemical synthesis as the standard. Next, the composition 1 was desalted by electrodialysis and optionally diluted to carry out its analysis to calculate the content from the detected amount of ion derived from each peptide. The results are shown in Table 2.

TABLE 2

| Amino Acid Sequences | Content in Composition 1 (μg/ml) |
| --- | --- |
| Asp-Arg-Pro | 154 |
| Asn-Trp | 2 |
| Val-Gly-Leu | 1 |
| Ile-Gly-Val | 2 |
| Gly-Val-Pro | 56 |
| pyroGlu-Pro | 60 |
| Tyr-Thr | 10 |
| Pro-Trp | 127 |

In the same manner, content of the peptides of the present invention contained in compositions obtained by production methods having different conditions are shown in Table 3. As comparative examples, wheat was used instead of soybean, and a protease agent for food use (Alcalase 2.4L-FG, manufactured by NOVOZYMES) instead of the *koji* fungus culture. From the results of Table 3, it can be understood that soybean is superior as the material; *koji* fungus culture is superior as the enzyme preparation; and 25° C. or more is superior as the reaction temperature. Namely, the peptides of the present invention can be produced particularly efficiently, by mixing and stirring soybean at 25° C. or more with the *koji* fungus culture.

TABLE 3

| Raw Material | Enzyme Preparation | Reaction Temperature | Asp-Arg-Pro (μg/ml) | Gly-Val-Pro (μg/ml) | Tyr-Thr (μg/ml) | Pro-Trp (μg/ml) | Remarks |
| --- | --- | --- | --- | --- | --- | --- | --- |
| Soybean | koji fungus culture | 20° C. | 33 | 21 | 1 | 90 | Present Invention 1 |
| Soybean | koji fungus culture | 25° C. | 47 | 26 | 3 | 181 | Present Invention 2 |
| Soybean | koji fungus culture | 30° C. | 80 | 37 | 4 | 185 | Present Invention 3 |
| Soybean | koji fungus culture | 35° C. | 95 | 42 | 4 | 161 | Present Invention 4 |
| Soybean | koji fungus culture | 50° C. | 154 | 56 | 10 | 127 | Present Invention 5 |
| Soybean | Alcalase | 35° C. | 3 | n.d. | 1 | 79 | Comparative Example 1 |
| Wheat | koji fungus culture | 35° C. | 3 | n.d. | 1 | 7 | Comparative Example 2 |

Example 3

Inspection of Hypotensive Action by Long-Term Administration of Mixed Feed to Rats After dividing 35 male salt-sensitive hypertensive rats (Dahl-S) of 5 weeks of age into 5 groups, each of which consisting of 7 animals, a long-term mixed feed administration test was carried out for 30 days. The salt concentration of samples was analyzed by a flame analysis and adjusted by adding salt such that the salt concentration in the feed became the same among respective groups. During the testing period, although the feed was ingested freely, the ingested amount was almost the same among respective groups.

First group (control) (▲ in the drawing): a feed prepared by mixing 25% v/w of a low salt soy sauce (salt concentration 7% w/v) based on the feed (salt concentration in the feed: 3% w/w).

Second group (composition 1) (● in the drawing): a feed prepared by mixing 20% v/v of the aforementioned composition 1 with the low salt soy sauce and mixing 25% v/w thereof based on the feed (salt concentration in the feed: 3% w/w and composition 1 concentration: 1.5% w/w).

Third group (a fraction obtained by removing peptides from the composition 1) (○ in the drawing): a feed prepared by mixing the aforementioned ODS-A fraction (a fraction hardly containing peptides, prepared by fractionating the composition 1 by an ODS column) with the low salt soy sauce and mixing 25% v/w thereof based on the feed (salt concentration in the feed: 3% w/w and ODS-A fraction concentration: 1.3% w/w).

Fourth group (a peptide fraction of the composition 1) (□ in the drawing): a feed prepared by mixing the aforementioned ODS-B fraction and ODS-C fraction (a fraction rich in peptides, prepared by fractionating the composition 1 by an ODS column) with the low salt soy sauce in response to the weight ratio and mixing 25% v/w thereof based on the feed (salt concentration in the feed: 3% w/w and total concentration of ODS-B and ODS-C fractions: 0.2% w/w).

Fifth group (a peptide fraction degraded by hydrochloric acid) (■ in the drawing): a feed prepared by completely degrading the ODS-B fraction and ODS-C fraction by hydrochloric acid degradation in accordance with the usual way and mixing the resulting peptides in the same manner as in the fourth group (salt concentration in the feed: 3% w/w and total concentration of ODS-B and ODS-C fractions: 0.2% w/w).

Figure 2:
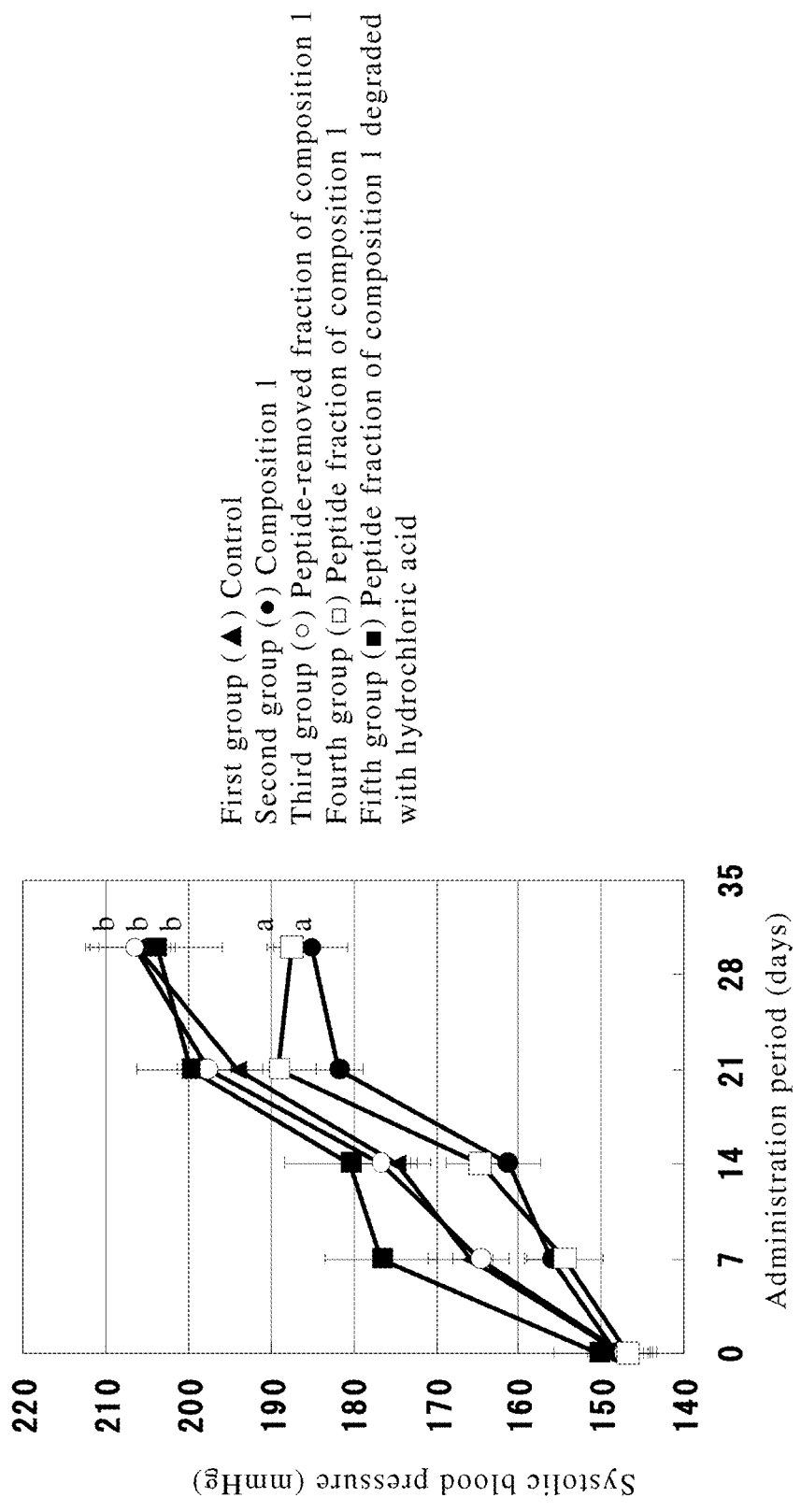
FIG. 2 is a figure showing changes in the blood pressure value when the composition 1 was administered to high blood pressure rats for a prolonged period of time.

Using a noninvasive sphygmomanometer MK-2000, measurement of systolic blood pressure was carried out at an interval of one week from the time of commencement of the test. Results of these are shown in FIG. 2. In this connection, statistical treatment was carried out by Tukey's multiple comparison test using the systolic blood pressure value on the 30$^{th}$ day after the administration.

From the results of FIG. 2, the composition 1 containing the peptides of the present invention significantly inhibited increase of blood pressure. Additionally, while hypotensive action was found in the peptide-containing fractions, the hypotensive action was lost by the degradation of peptides. Therefore, it was shown that the hypotensive action of composition 1 is derived from peptides.

Example 4

Sensory Evaluation

The sensory evaluation was carried out using the composition 1 and Comparative Example 1 described in Example 2. By a panel of 8 members, "strength of bitterness" and "desirableness of taste" were evaluated by a paired comparison method. From the results of Table 4, it can be understood that although the fermented seasoning of the present invention is rich in peptides, it shows less bitterness and has a suitable taste. Although a large number of peptide production methods which use protease agents have so far been disclosed, it is considered that the present invention is superior to the related art in terms of its taste.

TABLE 4

| | Sample which shows strong bitterness | Sample which has preferable taste |
|---|---|---|
| Composition 1 | 1 | 8 |
| Comparative Example 1 | 7 | 0 |

While the present invention has been described in detail and with reference to specific embodiments thereof, it will be apparent to one skilled in the art that various changes and modifications can be made therein without departing from the spirit and scope of the present invention.

This application is based on a Japanese patent application filed on Jan. 19, 2009 (Japanese Patent Application No. 2009-008503), the entire contents thereof being thereby incorporated by reference. Additionally, all of the references cited herein are incorporated as a whole.

INDUSTRIAL APPLICABILITY

The angiotensin converting enzyme inhibitory peptides obtained by the present invention effectively inhibit ACE by a small amount of ingestion and have no fear of causing side effects and can be orally ingested easily during daily life by persons having high blood pressure. Additionally, by the presentation of the production methods of compositions which contain said peptides; are excellent in taste; have high safety; and can be easily ingested as food, it becomes possible to greatly contribute to the improvement of quality of life of persons having high blood pressure.

The invention claimed is:

1. A composition for food and drink, said composition comprising a peptide having the amino acid sequence Asp-Arg-Pro, wherein said peptide has an inhibitory action on an angiotensin-converting enzyme, wherein the concentration of the peptide in the composition is from 47 to 154 µg/ml, wherein the composition alleviates a symptom of high blood pressure, and wherein the peptide is produced by a solid *koji* culture.

2. A food or a drink having added thereto a peptide having the amino acid sequence Asp-Arg-Pro, wherein said peptide has an inhibitory action on an angiotensin-converting enzyme, wherein the concentration of the peptide in the food or the drink is from 47 to 154 µg/ml, wherein the peptide is produced by a solid *koji* culture, and wherein the food or the drink alleviates a symptom of high blood pressure.

3. A composition for food and drink, said composition comprising a peptide having the amino acid sequence Asp-Arg-Pro obtained by stifling and mixing soybean with a solid *koji* culture at the range of 25 to 50° C. or more, wherein the concentration of the peptide in the composition is regulated within the range of 47 to 154 µg/ml, wherein the composition alleviates a symptom of high blood pressure.

* * * * *